United States Patent
Miyatake et al.

(10) Patent No.: US 8,586,499 B2
(45) Date of Patent: Nov. 19, 2013

(54) METHOD FOR PRODUCING CATALYST FOR PREPARATION OF METHACRYLIC ACID AND METHOD FOR PREPARING METHACRYLIC ACID

(75) Inventors: Toshiaki Miyatake, Niihama (JP); Junji Shibata, Niihama (JP); Eiichi Shiraishi, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 358 days.

(21) Appl. No.: 12/912,504

(22) Filed: Oct. 26, 2010

(65) Prior Publication Data

US 2011/0105789 A1    May 5, 2011

(30) Foreign Application Priority Data

Oct. 30, 2009    (JP) .................. 2009-250299

(51) Int. Cl.
| | |
|---|---|
| *B01J 27/00* | (2006.01) |
| *B01J 27/19* | (2006.01) |
| *B01J 27/192* | (2006.01) |
| *B01J 27/198* | (2006.01) |
| *C07C 51/16* | (2006.01) |
| *C07C 51/235* | (2006.01) |

(52) U.S. Cl.
USPC ........... 502/211; 502/208; 502/209; 502/212; 562/531; 562/535; 562/542

(58) Field of Classification Search
USPC .......... 502/208, 209, 211, 212; 562/531, 535, 562/542
See application file for complete search history.

(56) References Cited

U.S. PATENT DOCUMENTS

| | | | |
|---|---|---|---|
| 4,558,028 A | 12/1985 | Tsuneki et al. | |
| 4,925,980 A * | 5/1990 | Matsumoto et al. | 562/534 |
| 5,225,389 A * | 7/1993 | Caillod et al. | 502/205 |
| 6,747,172 B1 * | 6/2004 | Motoyama et al. | 562/549 |
| 7,732,367 B2 * | 6/2010 | Stevenson et al. | 502/208 |
| 7,851,397 B2 * | 12/2010 | Liang et al. | 502/208 |
| 2007/0010394 A1 * | 1/2007 | Atsushi et al. | 502/200 |
| 2007/0021296 A1 | 1/2007 | Liang et al. | |
| 2007/0021629 A1 | 1/2007 | Stevenson et al. | |
| 2009/0259071 A1 | 10/2009 | Ohishi et al. | |
| 2011/0237821 A1 * | 9/2011 | Brazdil et al. | 558/321 |

FOREIGN PATENT DOCUMENTS

| | | |
|---|---|---|
| JP | 05-177141 A | 7/1993 |
| JP | 2002-233758 A | 8/2002 |
| JP | 2010-207694 A | 9/2010 |
| JP | 2010-207696 A | 9/2010 |

OTHER PUBLICATIONS

Office Action issued Aug. 23, 2011, in Japanese Patent Application No. 2009-250299 with English Translation.

Office Action issued Oct. 7, 2011, in Singapore Patent Application No. 201007713-9.

* cited by examiner

*Primary Examiner* — Patricia L Hailey
(74) *Attorney, Agent, or Firm* — Sughrue Mion, PLLC

(57) ABSTRACT

A method for producing a catalyst for the preparation of methacrylic acid comprising a heteropolyacid compound containing phosphorus, molybdenum and an element X selected from the group consisting of potassium, rubidium, cesium and thallium and having an atomic ratio of the element X to molybdenum of 0.5:12 to 2:12, which method comprises the steps of mixing aqueous slurry A containing starting compounds of the heteropolyacid compound in which an atomic ratio of the element X to molybdenum is from 2:12 to 4:12, and aqueous slurry B containing starting compounds of the heteropolyacid compound in which an atomic ratio of the element X to molybdenum is from 0:12 to 0.5:12 to form a slurry mixture; heat-treating the slurry mixture at a temperature of 100° C. or higher; drying the slurry mixture; and calcining the dried mixture.

8 Claims, No Drawings

METHOD FOR PRODUCING CATALYST FOR PREPARATION OF METHACRYLIC ACID AND METHOD FOR PREPARING METHACRYLIC ACID

FIELD OF THE INVENTION

The present invention relates to a method for producing a catalyst for the preparation of methacrylic acid which catalyst comprises a heteropolyacid compound containing phosphorus, molybdenum and at least one element selected from the group consisting of potassium, rubidium, cesium and thallium, and a method for preparing methacrylic acid using a catalyst obtained by such a production method.

BACKGROUND ART

Hitherto, methacrylic acid is industrially produced by a method comprising subjecting a raw material, for example, methacrolein to a vapor phase catalytic oxidation reaction using molecular oxygen. This method uses a catalyst comprising a heteropolyacid compound containing phosphorus and molybdenum. The yield of methacrylic acid in such a method is largely influenced by the performances of the catalyst used (e.g., a conversion and a selectivity). Therefore, the production methods of the catalyst comprising a heteropolyacid compound are variously studied in order to improve the performances of the catalyst.

For example, JP-A-05-177141 discloses 1) a method for producing a heteropolyacid catalyst containing phosphorus, molybdenum and cesium comprising the steps of drying an aqueous slurry containing phosphorus, molybdenum and cesium to form a solid heteropolyacid compound, suspending the resulting solid heteropolyacid compound in water to form a suspension, and then adding an aqueous solution of starting compounds for the catalyst containing phosphorus and molybdenum but no cesium to the suspension, followed by drying and calcining, and JP-A-2002 233758 discloses 2) a method for producing a catalyst for the synthesis of methacrylic acid comprising a heteropolyacid compound containing phosphorus, molybdenum and at least one element X selected from the group consisting of potassium, rubidium, cesium and thallium, which method comprises the steps of drying an aqueous slurry containing molybdenum, phosphorus and the element X to form a solid heteropolyacid compound having an atomic ratio of the element X to molybdenum of 2.5:12 to 12:12, and adding the heteropolyacid compound to an aqueous slurry which is separately prepared so as to have an atomic ratio of the element X to molybdenum of 0.05:12 to 0.4:12, followed by drying and calcining.

However, the catalysts for the preparation of methacrylic acid produced by the method 1) or 2) described above are not necessarily satisfactory in conversion and selectivity.

SUMMARY OF THE INVENTION

An object of the present invention is to provide a method for producing a catalyst for the preparation of methacrylic acid, with which methacrylic acid can be prepared at a high conversion and a high selectivity.

Another object of the present invention is to provide a method for preparing methacrylic acid at a high yield, using the catalyst produced by the above method of the present invention.

According to the first aspect, the present invention provides a method for producing a catalyst for the preparation of methacrylic acid comprising a heteropolyacid compound containing phosphorus, molybdenum and at least one element X selected from the group consisting of potassium, rubidium, cesium and thallium and having an atomic ratio of the element X to molybdenum (X:Mo) of 0.5:12 to 2:12, said method comprising the steps of:

mixing aqueous slurry A containing starting compounds of said heteropolyacid compound in which an atomic ratio of the element X to molybdenum (X:Mo) is from 2:12 to 4:12, and aqueous slurry B containing starting compounds of said heteropolyacid compound in which an atomic ratio of the element X to molybdenum (X:Mo) is from 0:12 to 0.5:12 to form a slurry mixture, heat-treating the slurry mixture at a temperature of 100° C. or higher, drying the slurry mixture, and calcining the dried mixture.

According to the second aspect, the present invention provides a method for producing a catalyst for the preparation of methacrylic acid comprising a heteropolyacid compound containing phosphorus, molybdenum and at least one element X selected from the group consisting of potassium, rubidium, cesium and thallium and having an atomic ratio of the element X to molybdenum (X:Mo) of 0.5:12 to 2:12, said method comprising the steps of:

mixing aqueous slurry A containing starting compounds of said heteropolyacid compound in which an atomic ratio of the element X to molybdenum (X:Mo) is from 2:12 to 4:12 and which is heat-treated at a temperature of 100° C. or higher, and aqueous slurry B containing starting compounds of said heteropolyacid compound in which an atomic ratio of the element X to molybdenum (X:Mo) is from 0:12 to 0.5:12 to form a slurry mixture, drying the slurry mixture, and calcining the dried mixture.

According to the third aspect, the present invention provides a method for producing a catalyst for the preparation of methacrylic acid comprising a heteropolyacid compound containing phosphorus, molybdenum and at least one element X selected from the group consisting of potassium, rubidium, cesium and thallium and having an atomic ratio of the element X to molybdenum (X:Mo) of 0.5:12 to 2:12, said method comprising the steps of:

mixing aqueous slurry A containing starting compounds of said heteropolyacid compound in which an atomic ratio of the element X to molybdenum (X:Mo) is from 2:12 to 4:12, and aqueous slurry B containing starting compounds of said heteropolyacid compound in which an atomic ratio of the element X to molybdenum (X:Mo) is from 0:12 to 0.5:12 and which is heat-treated at a temperature of 100° C. or higher to form a slurry mixture, drying the slurry mixture, and calcining the dried mixture.

The present invention can provide a catalyst for the preparation of methacrylic acid, with which methacrylic acid can be prepared at a good conversion and a good selectivity. Therefore, when such a catalyst is used, methacrylic acid can be prepared at a high yield.

DETAILED DESCRIPTION OF THE INVENTION

The method for producing a catalyst for the preparation of methacrylic acid according to the present invention produces a catalyst comprising a heteropolyacid compound containing phosphorus, molybdenum and at least one element X selected from the group consisting of potassium, rubidium, cesium and thallium. In the present invention, the catalyst may comprise a free heteropolyacid or a salt of a heteropolyacid.

Among these, a catalyst comprising an acidic salt (a partially neutralized salt) of a heteropolyacid is preferable, and a catalyst comprising an acidic salt of a Keggin type heteropolyacid is more preferable. Preferably, the heteropolyacid compound constituting the catalyst to be produced by the method of the present invention further contains vanadium, and at least one element selected from the group consisting of copper, arsenic, antimony, boron, silver, bismuth, iron, cobalt, lanthanum and cerium (hereinafter sometimes refers to as "element Y").

The heteropolyacid compound constituting a catalyst to be produced by the method of the present invention has an atomic ratio of the element X to molybdenum (X:Mo) in a rage of 0.5:12 to 2:12. In other words, in the method for producing a catalyst according to the present invention, the ratios of elements forming the catalyst in aqueous slurries A and B, which are described in detail later, and a mixing ratio of them are suitably adjusted so that the atomic ratio of the element X to molybdenum in the heteropolyacid compound constituting the resulting catalyst is within the range described above.

The heteropolyacid compound which constitutes the catalyst to be produced by the method of the present invention preferably has the following composition formula (1):

$$P_aMo_bV_cX_dY_eO_x \tag{1}$$

wherein P, Mo and V represent phosphorus, molybdenum and vanadium, respectively; X represents at least one element (element X) selected from the group consisting of potassium, rubidium, cesium and thallium; Y represents at least one element (element Y) selected from the group consisting of copper, arsenic, antimony, boron, silver, bismuth, iron, cobalt, lanthanum and cerium; 0 represents oxygen; a, b, c, d and e are numbers satisfying $0<a\leq3$, $0\leq c\leq3$, $0.5\leq d\leq2$ and $0\leq e\leq3$, when b is 12; and x is a value determined depending on the oxidation states of other elements.

According to the method for producing a catalyst according to the present invention, firstly, aqueous slurry A is prepared by mixing the starting compounds of the heteropolyacid compound and water so that an atomic ratio of the element X to molybdenum (X:Mo) is adjusted in a range of 2:12 to 4:12, preferably in a range of 2.5:12 to 3.5:12, while aqueous slurry B is prepared by mixing the starting compounds of the heteropolyacid compound and water so that an atomic ratio of the element X to molybdenum (X:Mo) is adjusted in a rage of 0:12 to 0.5:12, preferably in a range of 0:12 to 0.3:12.

Examples of the starting compounds each containing the respective element among the elements constituting the heteropolyacid compound include an oxo acid, an oxo acid salt, an oxide, a nitrate, a carbonate, a bicarbonate, a hydroxide and a halide of each element. Specific examples of a compound containing phosphorus include phosphoric acid, phosphates and the like, specific examples of a compound containing molybdenum include molybdic acid, molybdates such as ammonium molybdate, molybdenum oxide, molybdenum chloride and the like; specific examples of a compound containing vanadium include vanadic acid, vanadates (metavanadate) such as ammonium vanadate (ammonium metavanadate), vanadium oxide, vanadium chloride and the like, and specific examples of a compound containing the element X include oxides such as potassium oxide, rubidium oxide and cesium oxide, nitrates such as potassium nitrate, rubidium nitrate, cesium nitrate and thallium nitrate, carbonates such as potassium carbonate, rubidium carbonate and cesium carbonate, bicarbonates such as potassium hydrogen carbonate and cesium hydrogen carbonate, hydroxides such as potassium hydroxide, rubidium hydroxide and cesium hydroxide, halides such as potassium chloride, rubidium chloride, cesium fluoride, cesium chloride, cesium bromide and cesium iodide, and the like. Examples of a compound containing the element Y include an oxo acid, an oxo acid salt, an oxide, a nitrate, a carbonate, a hydroxide and a halide.

Each of aqueous slurries A and B is prepared by mixing the respective starting compounds and water so that the atomic ratio of the element X to molybdenum (X:Mo) in the respective slurry is within the respective range described above.

In the preparation of each of aqueous slurries A and B, at least a compound comprising molybdenum is used as a starting compound of the heteropolyacid compound, and a compound comprising the element X is used in such an amount that the atomic ratio of the element X to molybdenum (X:Mo) falls in the range described above. Therefore, when the atomic ratio X:Mo is 0:12 in aqueous slurry B, no starting compound comprising the element X is used. Any compound that contains a constituting element other than molybdenum and the element X may be added to each of aqueous slurries A and B.

Ion-exchange water is usually used as water to be mixed with the starting compounds of the heteropolyacid compound in the preparation of each of aqueous slurries A and B. The amount of water mixed is usually 1 to 20 parts by weight per one part by weight of molybdenum in the resulting slurry.

When each of aqueous slurries A and B is prepared, it is preferable to supply a nitrate ion and an ammonium ion from the viewpoint of the improvement of a conversion and a selectivity of a catalyst produced.

During the preparation of each of aqueous slurries A and B, for supplying the nitrate ion, for example, nitric acid and a nitrate such as ammonium nitrate may be used as a nitrate ion source, besides the nitrates containing the elements which constitute the heteropolyacid compound. For supplying the ammonium ion, for example, ammonia and an ammonium salt such as ammonium nitrate, ammonium carbonate, ammonium hydrogen carbonate and ammonium acetate may be used as an ammonium ion source, besides the ammonium salts containing the elements which constitute the heteropolyacid compound. Preferably, the nitrates and ammonium salts containing the elements which constitute the heteropolyacid compound are used as the nitrate ion sources and the ammonium ion sources. More preferably, nitric acid, ammonia and ammonium nitrate are used so as to adjust the ratio of the nitrate ion and the ammonium ion in a range described below.

In aqueous slurry A, the proportions of the nitrate ion and the ammonium ion are preferably adjusted so that 1.0 to 3.0 moles of the ammonium ion is present per one mole of the nitrate ion. When the proportion of the ammonium ion is outside the above range, an effect for satisfactorily improving the catalytic activity (a conversion and a selectivity) may not be attained. In aqueous slurry B, the proportions of the nitrate ion and the ammonium iron may not be particularly limited and they may be adequately set.

When each of aqueous slurries A and B is prepared, the mixing order of each component is not particularly limited and may be arbitrarily set.

In the method for producing the catalyst according to the present invention, next, aqueous slurry A and aqueous slurry B are mixed. The amounts of aqueous slurries A and B are selected so that the atomic ratio of the element X to molybdenum (X:Mo) in the heteropolyacid constituting the finally obtained catalyst is in the range of 0.5:12 to 2:12 by taking into account the amounts of molybdenum and the element X contained in aqueous slurries A and B.

In the first method for producing the catalyst for the preparation of methacrylic acid according to the present invention, the mixed aqueous slurry obtained by mixing aqueous slurries A and B (hereinafter, sometimes, referred to as aqueous slurry M) is heat-treated at a temperature of 100° C. or higher, followed by drying and calcining it. The aqueous slurry A and/or B may be heat-treated at a temperature of 100° C. or higher prior to mixing the aqueous slurries A and B. In the first method, aqueous slurry A which has been heat-treated at a temperature of 100° C. or higher may be mixed with aqueous slurry B, or aqueous slurry A may be mixed with aqueous slurry B which has been heat-treated at a temperature of 100° C. or higher, or aqueous slurry A which has been heat-treated at a temperature of 100° C. or higher may be mixed with aqueous slurry B which has been heat-treated at a temperature of 100° C. or higher.

In the second method for producing the catalyst for the preparation of methacrylic acid according to the present invention, a mixed aqueous slurry obtained by mixing aqueous slurry A which has been heat-treated at a temperature of 100° C. or higher with aqueous slurry B is dried and then calcined. In the second method, aqueous slurry A which has been heat-treated at a temperature of 100° C. or higher may be mixed with aqueous slurry B which has been heat-treated at a temperature of 100° C. or higher.

In the third method for producing the catalyst for the preparation of methacrylic acid according to the present invention, a mixed aqueous slurry obtained by mixing aqueous slurry A with aqueous slurry B which has been heat-treated at a temperature of 100° C. or higher is dried and then calcined.

Each method for producing the catalyst for the preparation of methacrylic acid according to the present invention can produce a catalyst achieving a good conversion and a good selectivity.

A temperature and stirring conditions for mixing aqueous slurries A and B are not particularly limited and adequately selected. The mixing order of the aqueous slurries A and B may be adequately set. When either one of aqueous slurries A and B is already heat-treated, preferably an aqueous slurry which is not heat-treated is added to an aqueous slurry which is already heat-treated. When aqueous slurries A and B are both already heat-treated, preferably, heat-treated aqueous slurry B is added to heat-treated aqueous slurry A. When aqueous slurries A and B are not heat-treated, preferably, aqueous slurry B is added to aqueous slurry A.

Herein, "heat-treating" means that a slurry is heated and aged in a closed vessel. A heating temperature in the heat-treating step is preferably from 100 to 200° C., more preferably from 100 to 150° C. A heating method is not particularly limited. Usually, an aqueous slurry is charged in a reaction vessel such as an autoclave and then stirred in a closed state while heating the slurry at a temperature described above. A heating time in the heat-treating step is usually at least 0.1 hour, preferably at least 2 hours from the viewpoint of a catalyst activity of the catalyst produced, while the heating time is preferably 20 hours or less from the viewpoint of the productivity of the catalyst. A pressure in the heat-treating step is usually from 0.10 to 2.0 MPa, preferably from 0.11 to 0.60 MPa. Such a pressure may be achieved by a water vapor pressure and so on, which is generated in the closed vessel by water contained in the aqueous slurries under the above temperature condition, although it may be adjusted by pressurizing the reaction vessel with an inert gas such as nitrogen and helium, or with air.

When aqueous slurries A and B are mixed, or when or after aqueous slurry A or aqueous slurry B or aqueous slurry M is heat-treated (aged) as described above, a compound containing an element constituting the catalyst, in particular, a compound containing the element Y may be mixed, if necessary. In such a case, it is preferable to add the compound containing an element constituting the catalyst in the form of an aqueous suspension of such a compound.

In the method for producing a catalyst according to the present invention, aqueous slurry M as such or having been heated is then dried. A method for drying aqueous slurry M is not particularly limited, and a method usually used in this art field such as evaporation-to-dryness, spray drying, drum drying and flash drying may be adopted. A drying temperature is not particularly limited insofar as it is adequately set so that the water content in the resulting dried product is satisfactorily reduced. Usually, the drying temperature is lower than 300° C.

In the method for producing a catalyst according to the present invention, the dried product obtained by drying slurry M is subsequently calcined. The calcination can be carried out by a method usually used in this art field, and is not particularly limited. For example, it may be carried out in an atmosphere of oxidizing gas such as oxygen, or in an atmosphere of non-oxidizing gas such as nitrogen at a calcination temperature of, usually, 300° C. or higher. Preferably, the calcination is carried out by a multi-step process in an atmosphere of oxidizing gas or non-oxidizing gas from the viewpoint of a catalyst life. More preferably, a two-step process comprising the first calcination step which is carried out in an atmosphere of oxidizing gas and the second calcination step which is carried out in an atmosphere of non-oxidizing gas is employed.

The oxidizing gas used in the calcination step contains an oxidizing material. A preferred example of such a gas is oxygen-containing gas. The concentration of oxygen in the oxygen-containing gas is usually from about 1 to about 30% by volume. As a source of oxygen, an air or pure oxygen may be used, and it may be diluted with an inert gas, if necessary. The oxidizing gas may optionally contain water. However, the concentration of water in the oxidizing gas is usually 10% by volume or less. The oxidizing gas is preferably an air. Usually, the calcination carried out in the atmosphere of the oxidizing gas is carried out in the stream of the oxidizing gas. A temperature in the calcination step carried out in the atmosphere of the oxidizing gas is usually from 360 to 410° C., preferably from 380 to 400° C.

The non-oxidizing gas used in the calcination step contains substantially no oxidizing material such as oxygen. Specific examples of the non-oxidizing gas include inert gas such as nitrogen, carbon dioxide, helium, argon, etc. The non-oxidizing gas may optionally contain water. However, the concentration of water in the non-oxidizing gas is usually 10% by volume or less. In particular, nitrogen gas is preferably used as a non-oxidizing gas. Usually, the calcination carried out in the atmosphere of the non-oxidizing gas is carried out in the stream of the non-oxidizing gas. A temperature in the calcination step carried out in the atmosphere of the non-oxidizing gas is usually from 420 to 500° C., preferably from 420 to 450° C.

Prior to the calcination step, the dried product obtained after drying is preferably heat-treated (pre-calcined) in an atmosphere of oxidizing gas or non-oxidizing gas at a temperature of about 180 to 300° C.

The dried product obtained after drying may be molded into a desired shape such as a ring, a pellet, a sphere, a cylinder and the like before calcination or pre-calcination, if necessary. The molding may be carried out by any conventional method such as tableting or extrusion molding. For molding, water, a molding aid or a pore-forming agent may be added to the dried product, if necessary. Examples of the molding aid include ceramic fiber and glass fiber, and also ammonium nitrate. In particular, ammonium nitrate is preferably used since it functions as a pore-forming agent besides a molding aid.

Preferably, the molded product obtained by the previous molding process is subsequently subjected to temperature-humidity conditioning. When the molded product is subjected to the temperature-humidity conditioning before calcination or pre-calcination, a more stable catalyst can be obtained. In particular, the temperature-humidity conditioning is carried out by exposing the molded product to an atmosphere having a temperature of 40 to 100° C. and a relative humidity of 10 to 60% for about 0.5 to 10 hours. The conditioning may be carried out, for example, in a container having controlled temperature and humidity, or by blowing a gas having controlled temperature and humidity to the molded catalyst. An air is usually used as an atmosphere gas when carrying out the conditioning, while an inert gas such as nitrogen may be used.

The catalyst produced by the method of the present invention achieves a high conversion and a high selectivity, when it is used in the preparation of methacrylic acid by the gas phase catalytic oxidation of, for example, methacrolein with molecular oxygen.

The method for preparing methacrylic acid according to the present invention comprises the steps of producing the catalyst by the catalyst-production method of the present invention, and subjecting a compound selected from the group consisting of methacrolein, isobutyl aldehyde, isobutane and isobutyric acid (hereinafter sometimes referred to as "raw material for methacrylic acid") to a gas phase catalytic oxidation reaction in the presence of such a catalyst. Methacrylic acid can be prepared in a high conversion and a high selectivity using the catalyst which is produced by the catalyst-production method of the present invention.

Methacrylic acid is usually prepared by charging the catalyst in a fixed-bed multitubular reactor and supplying a starting gas mixture containing oxygen and the raw material for methacrylic acid, although a reaction system such as a fluidized bed or a moving bed may also be used. As an oxygen source, an air is usually used. Besides oxygen and the raw material for methacrylic acid, the starting gas mixture may contain nitrogen, carbon dioxide, carbon monoxide, water vapor, etc.

The raw material for methacrylic acid may not necessarily be a purified material with a high purity. For example, methacrolein may be a methacrolein-containing reaction product gas obtained by a gas phase catalytic oxidization reaction of isobutylene or tert-butyl alcohol. The starting gas mixture may contain one raw material for methacrylic acid or two or more raw materials for methacrylic acid.

The reaction conditions of the method for preparing methacrylic acid may arbitrarily selected depending on the kind of the raw material for methacrylic acid contained in the starting gas mixture, etc. For example, when methacrolein is used as a raw material, the reaction is carried out usually under conditions such that a concentration of methacrolein in the starting gas mixture is 1 to 10% by volume, the concentration of water vapor is 1 to 30% by volume, a molar ratio of oxygen to methacrolein is 1 to 5, a space velocity is 500 to 5000 $h^{-1}$ (based on the normal state), a reaction temperature is 250 to 350° C., and a reaction pressure is 0.1 to 0.3 MPa. When isobutane is used as a raw material for methacrylic acid, the reaction is carried out usually under conditions such that a concentration of isobutane in the starting gas is 1 to 85% by volume, a water vapor concentration is 3 to 30% by volume, a molar ratio of oxygen to isobutane is 0.05 to 4, a space velocity is 400 to 5000 $h^{-1}$ (based on the normal state), a reaction temperature is 250 to 400° C., and a reaction pressure is 0.1 to 1 MPa. When isobutylaldehyde or isobutyric acid is used as a raw material for methacrylic acid, substantially the same reaction conditions as those employed when methacrolein is used as the raw material are adopted.

EXAMPLES

Hereinafter, the present invention is explained in more detail by making reference to the Examples, which do not limit the scope of the present invention in any way.

An air used in the Examples contains 3.5% by volume of water (corresponding to the water content of an atmosphere), and nitrogen used in the Examples is substantially free of water.

The catalysts obtained in the following Examples were analyzed and evaluated as follows.

A catalyst composition (ratio of elements constituting catalyst) was determined by analyzing a catalyst by fluorescent X-ray analysis using a fluorescent X-ray analyzer, ZSX Primus II manufactured by Rigaku Corporation.

Activity Test of Catalyst

Nine grams (9 g) of a catalyst were charged into a glass micro-reactor having an inner diameter of 16 mm, and a starting gas composed of 4% by volume of methacrolein, 12% by volume of molecular oxygen, 17% by volume of water vapor and 67% by volume of nitrogen, prepared by mixing methacrolein, air, steam and nitrogen, was fed to the reactor at a space velocity of 670 $h^{-1}$, and a reaction was carried out at a furnace temperature (the temperature of a furnace used for heating the micro-reactor) of 355° C. for one hour. Then, the starting gas having the same composition as above was fed to the micro-reactor at the same space velocity as above, and the reaction was re-started at a furnace temperature of 280° C. After carrying out the reaction for 1 hour from the re-start of the reaction, an exit gas (a gas after reaction) was sampled and analyzed by gas chromatography, and a conversion of methacrolein (%), a selectivity of methacrylic acid (%) and a yield of methacrylic acid were calculated by the following equations.

Conversion of methacrolein(%)=[(moles of methacrolein reacted)/(moles of methacrolein fed)]×100

Selectivity of methacrylic acid(%)=[(moles of methacrylic acid generated)/(moles of methacrolein reacted)]×100

Yield(%)=[(Conversion of methacrolein)×(Selectivity of methacrylic acid)]/100

Example 1

Preparation of Aqueous Slurry A1

In 105 g of ion-exchange water heated to 40° C., 38.2 g of cesium nitrate [$CsNO_3$], 12.8 g of 75 wt % orthophosphoric acid, and 12.2 g of 67.5 wt % nitric acid were dissolved to form Liquid α. Separately, 138 g of ammonium molybdate tetrahydrate [$(NH_4)_6Mo_7O_{24}.4H_2O$] was dissolved in 154 g of ion-exchange water heated to 40° C., followed by suspending 3.82 g of ammonium metavanadate [$NH_4VO_3$] therein to form Liquid β. Liquid α was dropwise added to Liquid β while stirring and maintaining the temperatures of Liquids α and β at 40° C. to obtain Aqueous Slurry A1. The atomic ratios of metal elements, i.e., phosphorus, molybdenum, vanadium and cesium contained in Aqueous Slurry A1 were 1.5, 12, 0.5 and 3.0, respectively, and thus the atomic ratio of cesium to molybdenum was 3.0:12.

Preparation of Aqueous Slurry B1

In 120 g of ion-exchange water heated to 40° C., 14.6 g of 75 wt. % orthophosphoric acid and 13.9 g of 67.5 wt. % nitric acid were dissolved to form Liquid a. Separately, 158.2 g of ammonium molybdate tetrahydrate was dissolved in 176 g of ion-exchange water heated to 40° C., followed by suspending 4.37 g of ammonium metavanadate therein to form Liquid b. Liquid a was dropwise added to Liquid b while stirring and maintaining the temperatures of Liquids a and b at 40° C. to obtain Aqueous Slurry B1. The atomic ratios of the metal elements, i.e., phosphorus, molybdenum and vanadium contained in Aqueous Slurry B1 were 1.5, 12 and 0.5, respectively, and thus the atomic ratio of cesium to molybdenum was 0:12.

Preparation of Aqueous Slurry M1

The whole quantity of Aqueous Slurry B1 was mixed with the whole quantity of Aqueous Slurry A1, and then the mixture was stirred in a closed vessel at 120° C. for 5 hours. Then, to the mixture, the suspension of 10.2 g of antimony trioxide [$Sb_2O_3$] and 10.1 g of copper nitrate trihydrate [$Cu(NO_3)_2 \cdot 3H_2O$] in 23.4 g of ion-exchange water was added, and the mixture was further stirred in the closed vessel at 120° C. for 5 hours to obtain Aqueous Slurry M1.

Drying and Calcination of Aqueous Slurry M1

Aqueous Slurry M1 obtained in the previous step was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (1).

Catalyst (1) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (1) are shown in TABLE 1.

Example 2

Preparation of Aqueous Slurry A1 and Aqueous Slurry B1

Aqueous Slurry A1 and Aqueous Slurry B1 were prepared in the same manners as in EXAMPLE 1.

Preparation of Aqueous Slurry A2

Aqueous Slurry A1 was stirred in a closed vessel at 120° C. for 5 hours. Then, the suspension of 4.8 g of antimony trioxide and 4.7 g of copper nitrate trihydrate in 11.0 g of ion-exchange water was added thereto. Thereafter, the mixture was stirred in the closed vessel at 120° C. for 5 hours to obtain Aqueous Slurry A2. The atomic ratios of the metal elements, i.e., phosphorus, molybdenum, vanadium, antimony, copper and cesium contained in Aqueous Slurry A2 were 1.5, 12, 0.5, 0.5, 0.3 and 3.0, respectively, and thus the atomic ratio of cesium to molybdenum was 3.0:12.

Preparation of Aqueous Slurry M2

The whole quantity of Aqueous Slurry B1 was mixed with the whole quantity of Aqueous Slurry A2, and then the mixture was stirred in a closed vessel at 120° C. for 5 hours. Then, to the mixture, the suspension of 5.4 g of antimony trioxide and 5.4 g of copper nitrate trihydrate in 12.5 g of ion-exchange water was added, and the mixture was further stirred in the closed vessel at 120° C. for 5 hours to obtain Aqueous Slurry M2.

Drying and Calcination of Aqueous Slurry M2

Aqueous Slurry M2 obtained in the previous step was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (2).

Catalyst (2) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (2) are shown in TABLE 1.

Example 3

Preparation of Aqueous Slurry A1 and Aqueous Slurry B1

Aqueous Slurry A1 and Aqueous Slurry B1 were prepared in the same manners as in EXAMPLE 1.

Preparation of Aqueous Slurry B2

Aqueous Slurry B1 was stirred in a closed vessel at 120° C. for 5 hours. Then, the suspension of 5.4 g of antimony trioxide and 5.4 g of copper nitrate trihydrate in 12.5 g of ion-exchange water was added thereto. Thereafter, the mixture was stirred in the closed vessel at 120° C. for 5 hours to obtain Aqueous Slurry B2. The atomic ratios of the metal elements, i.e., phosphorus, molybdenum, vanadium, antimony and copper contained in Aqueous Slurry B2 were 1.5, 12, 0.5, 0.5 and 0.3, respectively, and thus the atomic ratio of cesium to molybdenum was 0:12.

Preparation of Aqueous Slurry M3

The whole quantity of Aqueous Slurry A1 was mixed with the whole quantity of Aqueous Slurry B2, and then the mixture was stirred in a closed vessel at 120° C. for 5 hours. Then, to the mixture, the suspension of 4.8 g of antimony trioxide and 4.7 g of copper nitrate trihydrate in 11.0 g of ion-exchange water was added, and the mixture was further stirred in a closed vessel at 120° C. for 5 hours to obtain aged Aqueous Slurry M3.

Drying and Calcination of Aqueous Slurry M3

Aqueous Slurry M3 obtained in the previous step was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (3).

Catalyst (3) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (3) are shown in TABLE 1.

Example 4

Preparation of Aqueous Slurry A2 and Aqueous Slurry B2

Aqueous Slurry A2 and Aqueous Slurry B2 were prepared in the same manners as in EXAMPLE 2 and EXAMPLE 3, respectively.

Preparation of Aqueous Slurry M4

The whole quantity of Aqueous Slurry B2 was mixed with the whole quantity of Aqueous Slurry A2, and then the mixture was stirred in a closed vessel at 120° C. for 5 hours to obtain Aqueous Slurry M4.

Drying and Calcination of Aqueous Slurry M4

Aqueous Slurry M4 obtained in the previous step was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (4).

Catalyst (4) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (4) are shown in TABLE 1.

Example 5

Preparation of Aqueous Slurry A2 and Aqueous Slurry B2

Aqueous Slurry A2 and Aqueous Slurry B2 were prepared in the same manners as in EXAMPLE 2 and EXAMPLE 3, respectively.

Preparation of Aqueous Slurry M5

The whole quantity of Aqueous Slurry B2 was mixed with the whole quantity of Aqueous Slurry A2 to obtain Aqueous Slurry M5.

Drying and Calcination of Aqueous Slurry M5

Aqueous Slurry M5 obtained in the previous step was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (5).

Catalyst (5) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (5) are shown in TABLE 1.

COMPARATIVE EXAMPLE 1

In 224 g of ion-exchange water heated to 40° C., 38.2 g of cesium nitrate, 27.4 g of 75 wt. % orthophosphoric acid and 26.1 g of 67.5 wt. % nitric acid were dissolved to form Liquid c. Separately, 297 g of ammonium molybdate tetrahydrate was dissolved in 330 g of ion-exchange water heated to 40° C., followed by suspending 8.19 g of ammonium metavanadate therein to form Liquid d.

Liquid c was dropwise added to Liquid d while stirring and maintaining the temperatures of Liquids c and d at 40° C., and then the mixture was further stirred in a closed vessel at 120° C. for 5 hours. Next, the suspension of 10.2 g of antimony trioxide and 10.1 g of copper nitrate trihydrate in 23.4 g of ion-exchange water was added to the mixture. Thereafter, the mixture was stirred in the closed vessel at 120° C. for 5 hours to obtain Aqueous Slurry C.

Aqueous Slurry C obtained in the previous step was dried by heating it an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (6).

The atomic ratios of the metal elements other than oxygen, i.e., phosphorus, molybdenum, vanadium, antimony, copper and cesium contained in Catalyst (6) were 1.5, 12, 0.5, 0.5, 0.3 and 1.4, respectively, and thus the atomic ratio of cesium to molybdenum was 1.4:12. The results of activity test of Catalyst (6) are shown in TABLE 1.

COMPARATIVE EXAMPLE 2

Preparation of Aqueous Slurry A1 and Aqueous Slurry B1

Aqueous Slurry A1 and Aqueous Slurry B1 were prepared in the same manners as in EXAMPLE 1.

Preparation of Aqueous Slurry D

The whole quantity of Aqueous Slurry B1 was mixed with the whole quantity of Aqueous Slurry A1, and then the suspension of 10.2 g of antimony trioxide and 10.1 g of copper nitrate trihydrate in 23.4 g of ion-exchange water was added thereto to obtain Aqueous Slurry D.

Drying and Calcination of Aqueous Slurry D

Aqueous Slurry D obtained in the previous step was dried by heating it in an air at 135° C. to evaporate water therefrom. To 100 parts by weight of the dried product, 4 parts by weight of ceramic fiber, 17 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (7).

Catalyst (7) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (7) are shown in TABLE 1.

COMPARATIVE EXAMPLE 3

Preparation of Heteropolyacid Compound S

In 224 g of ion-exchange water heated to 40° C., 81.8 g of cesium nitrate, 27.4 g of 75 wt. % orthophosphoric acid and 38.2 g of 67.5 wt. % nitric acid were dissolved to form Liquid e. Separately, 297 g of ammonium molybdate tetrahydrate was dissolved in 330 g of ion-exchange water heated to 40° C., followed by suspending 8.19 g of ammonium metavanadate therein to form Liquid f.

Liquid e was dropwise added to Liquid f while stirring and maintaining the temperatures of Liquids e and f at 40° C., and then the mixture was further stirred in a closed vessel at 120° C. for 5 hours. Next, the suspension of 10.2 g of antimony trioxide and 10.1 g of copper nitrate trihydrate in 23.4 g of ion-exchange water was added to the mixture. Thereafter, the mixture was stirred in a closed vessel at 120° C. for 5 hours to obtain a slurry. The resulting slurry was dried by heating it in an air at 135° C. for 18 hours and the dried product was heated in an air at 250° C. for 1 hour to obtain solid Heteropolyacid Compound S.

The atomic ratios of the metal elements other than oxygen, i.e., phosphorus, molybdenum, vanadium, antimony, copper and cesium contained in Heteropolyacid Compound S were 1.5, 12, 0.5, 0.5, 0.3 and 3.0, respectively, and thus the atomic ratio of cesium to molybdenum was 3.0:12.

the suspension of 3.53 g of antimony trioxide and 3.53 g of copper nitrate trihydrate in 7.9 g of ion-exchange water was added to the mixture. Thereafter, the mixture was stirred in the closed vessel at 120° C. for 5 hours to obtain a mixed slurry. The resulting mixed slurry was dried at 135° C. To 100 parts by weight of the dried product, 4 parts by weight of ceramic fiber, 18 parts by weight of ammonium nitrate and 7.5 parts by weight of ion-exchange water were added, and the mixture was kneaded and extrusion-molded into cylinders each having a diameter of 5 mm and a height of 6 mm. The molded cylinders were dried at 90° C. and a relative humidity of 30% for 3 hours and then calcined by maintaining them in an air stream at 390° C. for 4 hours and then in a nitrogen stream at 435° C. for 4 hours to obtain Catalyst (8).

Catalyst (8) comprised a heteropolyacid compound, and the atomic ratios of the metal elements other than oxygen, i.e., phosphorus, molybdenum, vanadium, antimony, copper and cesium contained in the heteropolyacid compound were 1.5, 12, 0.5, 0.5, 0.3 and 1.4, respectively, and thus the atomic ratio of cesium to molybdenum was 1.4:12. The results of activity test of Catalyst (8) are shown in TABLE 1.

TABLE 1

|  | Application of Heat Treatment | | | Activity Test | | |
| --- | --- | --- | --- | --- | --- | --- |
|  | Aqueous slurry A | Aqueous slurry B | Aqueous slurry M | Conversion (%) | Selectivity (%) | Yield (%) |
| Example 1 Catalyst (1) | No | No | Yes | 96 | 78 | 75 |
| Example 2 Catalyst (2) | Yes | No | Yes | 97 | 77 | 75 |
| Example 3 Catalyst (3) | No | Yes | Yes | 97 | 79 | 77 |
| Example 4 Catalyst (4) | Yes | Yes | Yes | 96 | 80 | 77 |
| Example 5 Catalyst (5) | Yes | Yes | No | 95 | 78 | 74 |
| Comp. Ex. 1 Catalyst (6) |  | *1) |  | 93 | 79 | 73 |
| Comp. Ex. 2 Catalyst (7) | No | No | No | 80 | 85 | 68 |
| Comp. Ex. 3 Catalyst (8) | (Dried product) | No | Yes | 90 | 81 | 73 |

Note:
1) Without distributing the starting compounds in Aqueous Slurries A and B, the starting compounds were all together mixed with water so that the atomic ratio of cesium to molybdenum was 1.4:12, and then the mixture was heated.

Preparation of Aqueous Slurry E

In 150 g of ion-exchange water heated to 40° C., 9.48 g of 75 wt. % orthophosphoric acid, 9.03 g of 67.5 wt. % nitric acid and 20.1 g of ammonium nitrate were dissolved to form Liquid g. Separately, 103 g of ammonium molybdate tetrahydrate was dissolved in 220 g of ion-exchange water heated to 40° C., followed by suspending 2.83 g of ammonium metavanadate therein to form Liquid h.

Liquid g was dropwise added to Liquid h while stirring and maintaining the temperatures of Liquids g and h at 40° C. to obtain Aqueous Slurry E. The atomic ratios of the metal elements, i.e., phosphorus, molybdenum and vanadium contained in Aqueous Slurry E were 1.5, 12 and 0.5, respectively, while the atomic ratios of antimony, copper and cesium were all 0. Thus, the atomic ratio of cesium to molybdenum was 0:12.

Mixing of Heteropolyacid Compound S and Aqueous Slurry E

With the whole quantity of Aqueous Slurry E, 99.2 g of Heteropolyacid Compound S was mixed, and then the mixture was stirred in a closed vessel at 120° C. for 5 hours. Next,

The invention claimed is:

1. A method for producing a catalyst for the preparation of methacrylic acid comprising a heteropolyacid compound containing phosphorus, molybdenum and at least one element X selected from the group consisting of potassium, rubidium, cesium and thallium and having an atomic ratio of the element X to molybdenum (X:Mo) of 0.5:12 to 2:12, said method comprising the steps of:
    mixing aqueous slurry A containing starting compounds of said heteropolyacid compound in which an atomic ratio of the element X to molybdenum (X:Mo) is from 2:12 to 4:12, and aqueous slurry B containing starting compounds of said heteropolyacid compound in which an atomic ratio of the element X to molybdenum (X:Mo) is from 0:12 to 0.5:12 to form a slurry mixture,
    heat-treating the slurry mixture at a temperature of 100° C. or higher in a closed vessel,
    drying the slurry mixture, and
    calcining the dried mixture.

2. The method according to claim 1, wherein said aqueous slurry A is heat-treated at a temperature of 100° C. or higher in the closed vessel.

3. The method according to claim 1, wherein said aqueous slurry B is heat-treated at a temperature of 100° C. or higher in the closed vessel.

4. A method for producing a catalyst for the preparation of methacrylic acid comprising a heteropolyacid compound containing phosphorus, molybdenum and at least one element X selected from the group consisting of potassium, rubidium, cesium and thallium and having an atomic ratio of the element X to molybdenum (X:Mo) of 0.5:12 to 2:12, said method comprising the steps of:

mixing aqueous slurry A containing starting compounds of said heteropolyacid compound in which an atomic ratio of the element X to molybdenum (X:Mo) is from 2:12 to 4:12 and which is heat-treated at a temperature of 100° C. or higher in a closed vessel, and aqueous slurry B containing starting compounds of said heteropolyacid compound in which an atomic ratio of the element X to molybdenum (X:Mo) is from 0:12 to 0.5:12 to form a slurry mixture, drying the slurry mixture, and calcining the dried mixture.

5. The method according to claim 4, wherein said aqueous slurry B is heat-treated at a temperature of 100° C. or higher in a closed vessel.

6. The method according to claim 1, wherein said heteropolyacid constituting the catalyst for the preparation of methacrylic acid further comprises vanadium, and at least one element selected from the group consisting of copper, arsenic, antimony, boron, silver, bismuth, iron, cobalt, lanthanum and cerium.

7. A method for preparing methacrylic acid comprising the steps of:

producing a catalyst for the preparation of methacrylic acid by the method according to claim 1 and then subjecting at least one compound selected from the group consisting of methacrolein, isobutylaldehyde, isobutane and isobutyric acid to a gas phase catalytic oxidation reaction in the presence of said catalyst.

8. A method for producing a catalyst for the preparation of methacrylic acid comprising a heteropolyacid compound containing phosphorus, molybdenum and at least one element X selected from the group consisting of potassium, rubidium, cesium and thallium and having an atomic ratio of the element X to molybdenum (X:Mo) of 0.5:12 to 2:12, said method comprising the steps of:

mixing aqueous slurry A containing starting compounds of said heteropolyacid compound in which an atomic ratio of the element X to molybdenum (X:Mo) is from 2:12 to 4:12, and aqueous slurry B containing starting compounds of said heteropolyacid compound in which an atomic ratio of the element X to molybdenum (X:Mo) is from 0:12 to 0.5:12 and which is heat-treated at a temperature of 100° C. or higher in a closed vessel to form a slurry mixture, drying the slurry mixture, and calcining the dried mixture.

* * * * *